United States Patent
Funamura et al.

(10) Patent No.: US 10,775,252 B2
(45) Date of Patent: Sep. 15, 2020

(54) MEDICAL LIQUID-PRESSURE-DETECTING DEVICE

(71) Applicant: Nikkiso Company Limited, Tokyo (JP)

(72) Inventors: Shigeaki Funamura, Shizuoka (JP); Hiroaki Mochizuki, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 424 days.

(21) Appl. No.: 15/823,794

(22) Filed: Nov. 28, 2017

(65) Prior Publication Data
US 2018/0080843 A1 Mar. 22, 2018

Related U.S. Application Data

(63) Continuation of application No. PCT/JP2016/066177, filed on Jun. 1, 2016.

(30) Foreign Application Priority Data

Jun. 1, 2015 (JP) .................. 2015-111354

(51) Int. Cl.
*A61M 1/36* (2006.01)
*G01L 7/08* (2006.01)
(Continued)

(52) U.S. Cl.
CPC .............. *G01L 7/088* (2013.01); *A61B 5/021* (2013.01); *A61B 5/6866* (2013.01); *A61M 1/16* (2013.01);
(Continued)

(58) Field of Classification Search
None
See application file for complete search history.

(56) References Cited

U.S. PATENT DOCUMENTS

| 8,092,414 B2 | 1/2012 | Schnell et al. |
| 8,960,010 B1 | 2/2015 | Crnkovich et al. |

(Continued)

FOREIGN PATENT DOCUMENTS

| EP | 0330891 A1 | 9/1989 |
| WO | 2014/028103 A1 | 2/2014 |
| WO | 2014/093846 A1 | 6/2014 |

OTHER PUBLICATIONS

International Search Report for Application No. PCT/JP2016/066177 dated Aug. 30, 2016.
(Continued)

*Primary Examiner* — Peter J Macchiarolo
*Assistant Examiner* — Mohammed E Keramet-Amircolai
(74) *Attorney, Agent, or Firm* — Young Basile Hanlon & MacFarlane, P.C.

(57) ABSTRACT

A medical liquid-pressure-detecting device capable of detecting both the negative and positive pressure of liquid, whereby the misconnection of the device to a liquid flow route can be prevented. A medical liquid-pressure-detecting device includes a chamber unit having an inlet that liquid flowing in a flow route is taken in and an outlet that the liquid is discharged, the chamber unit storing the liquid by a predetermined amount; and a diaphragm dividing the chamber unit into a liquid chamber and a gas chamber, the diaphragm being deformable in accordance with a pressure of the liquid, the medical liquid-pressure-detecting device detecting a pressure of liquid in the flow route on the basis of a change in the pressure in the gas chamber that is caused by the deformation of the diaphragm that includes a negative-pressure-detecting region that deforms toward one side when a negative pressure is generated in the liquid stored in the liquid chamber, and a positive-pressure-detecting region
(Continued)

that deforms toward an other side when a positive pressure is generated in the liquid chamber.

20 Claims, 11 Drawing Sheets

(51) Int. Cl.
| | | |
|---|---|---|
| *G01L 19/00* | (2006.01) | |
| *A61B 5/00* | (2006.01) | |
| *A61B 5/021* | (2006.01) | |
| *A61M 1/16* | (2006.01) | |
| *A61M 1/34* | (2006.01) | |

(52) U.S. Cl.
CPC ........ *A61M 1/3639* (2013.01); *A61M 1/3641* (2014.02); *G01L 19/0046* (2013.01); *A61M 1/3403* (2014.02); *A61M 1/3607* (2014.02); *A61M 2205/3331* (2013.01)

(56) References Cited

U.S. PATENT DOCUMENTS

| | | | | |
|---|---|---|---|---|
| 2003/0115965 | A1* | 6/2003 | Mittelstein | G01L 9/0064 73/706 |
| 2007/0118153 | A1* | 5/2007 | Funamura | A61B 17/0485 606/148 |
| 2007/0295093 | A1* | 12/2007 | Reiter | A61M 1/3641 73/706 |
| 2017/0312412 | A1* | 11/2017 | Mochizuki | A61M 1/1658 |
| 2017/0340798 | A1* | 11/2017 | Lindley | G01L 7/082 |

OTHER PUBLICATIONS

Extended European Search Report dated Feb. 4, 2019, Application No. EP16803378.5.

\* cited by examiner

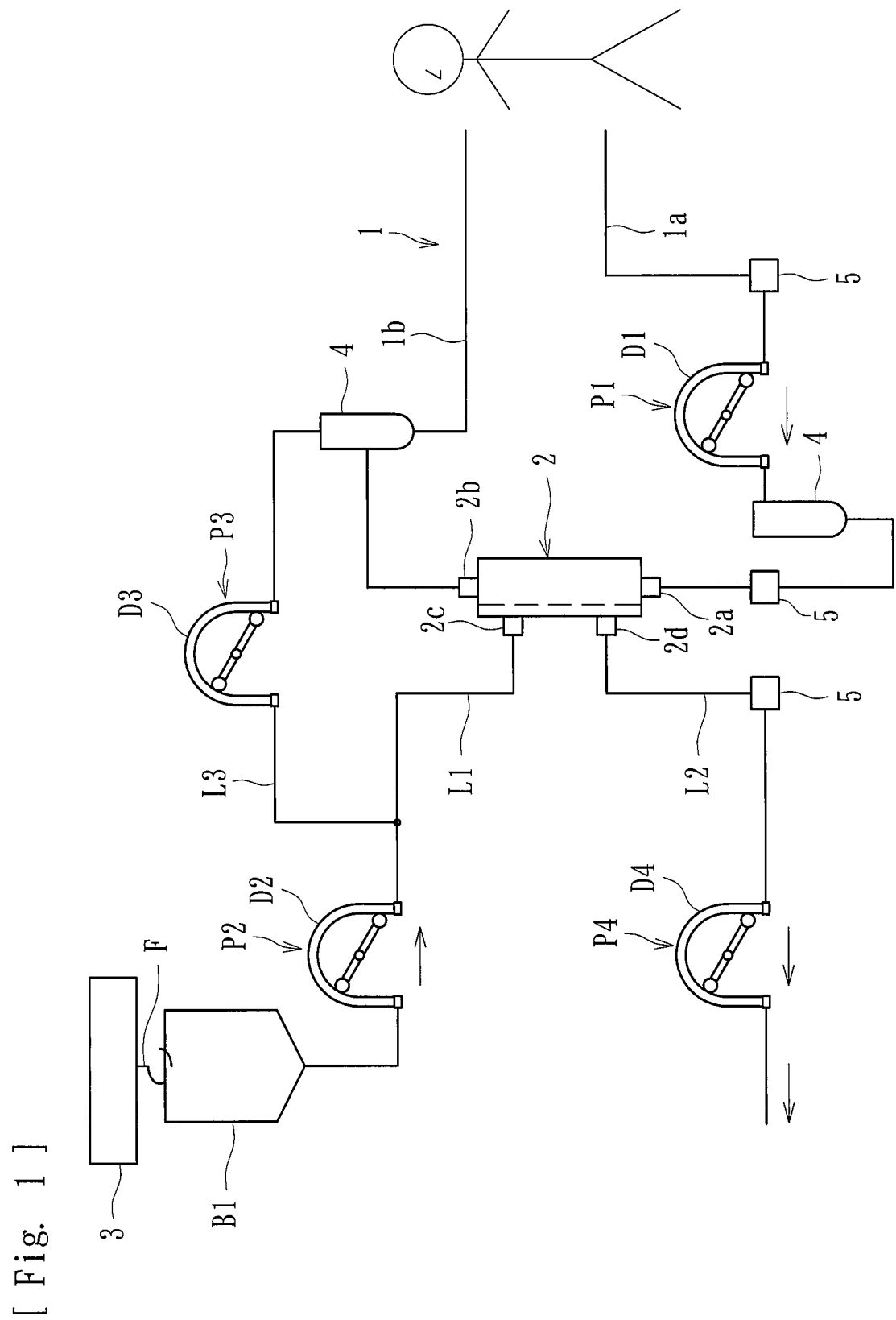
[Fig. 1]

[Fig. 2]
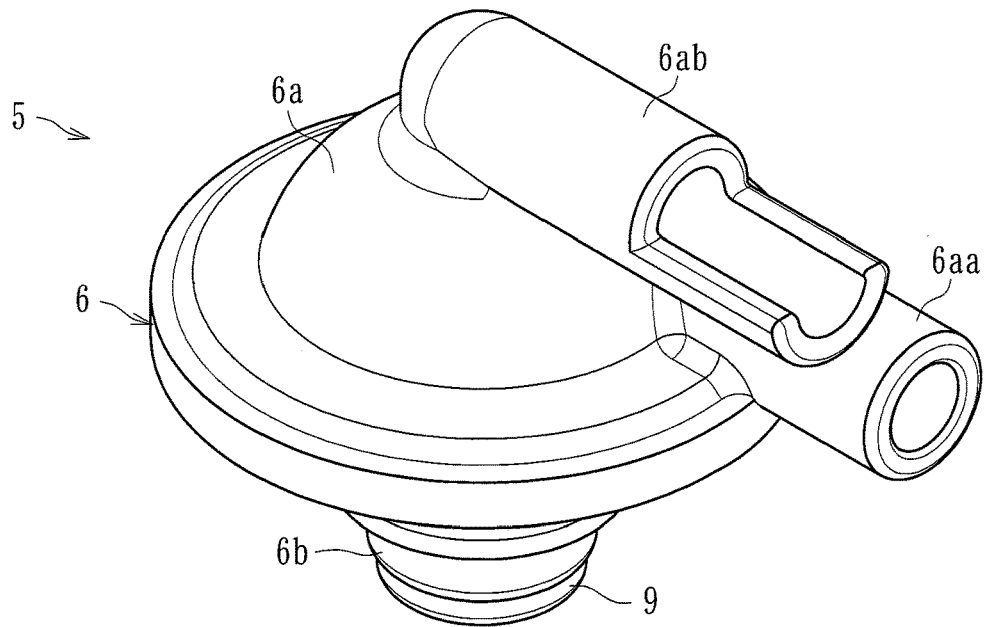
[Fig. 3]
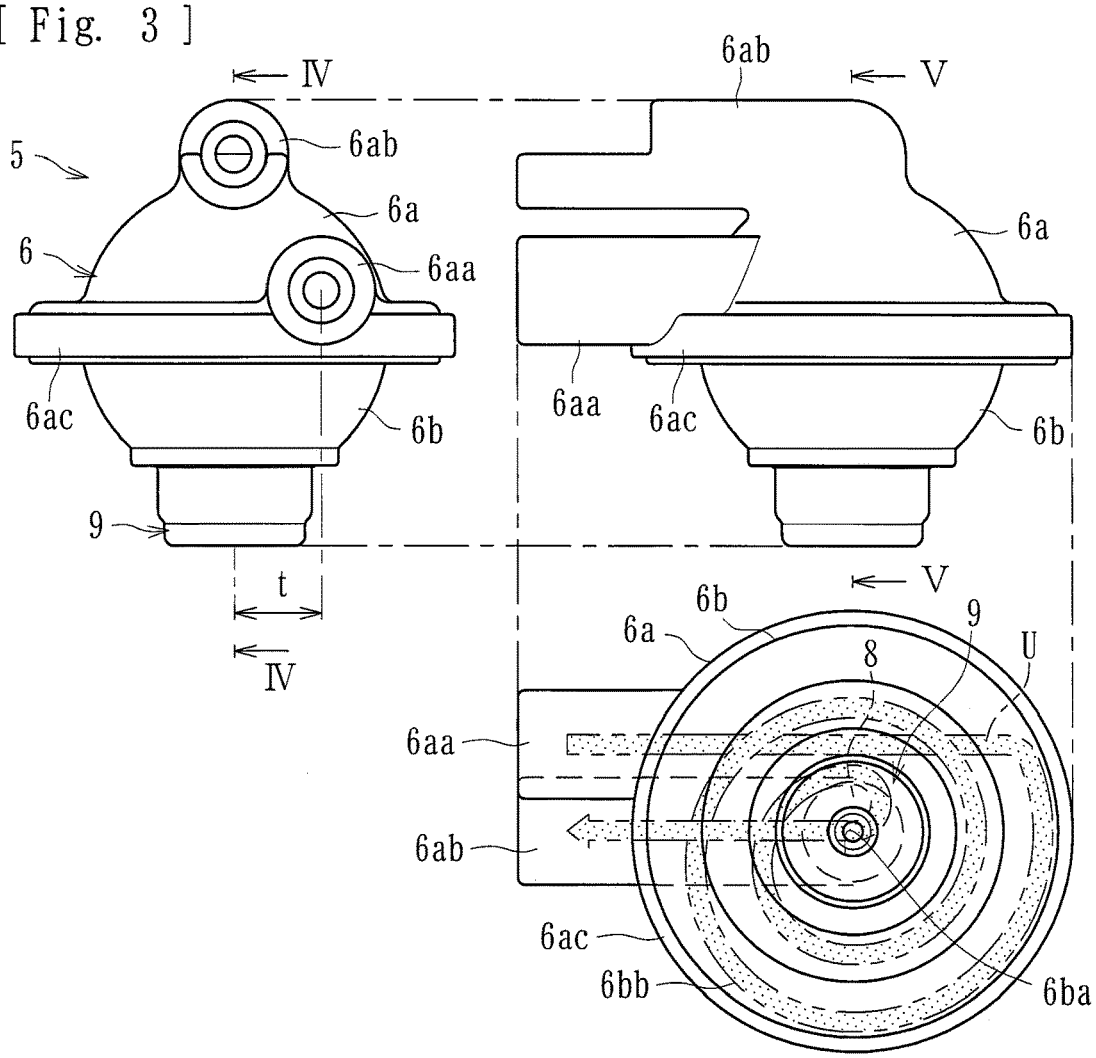

[Fig. 4]
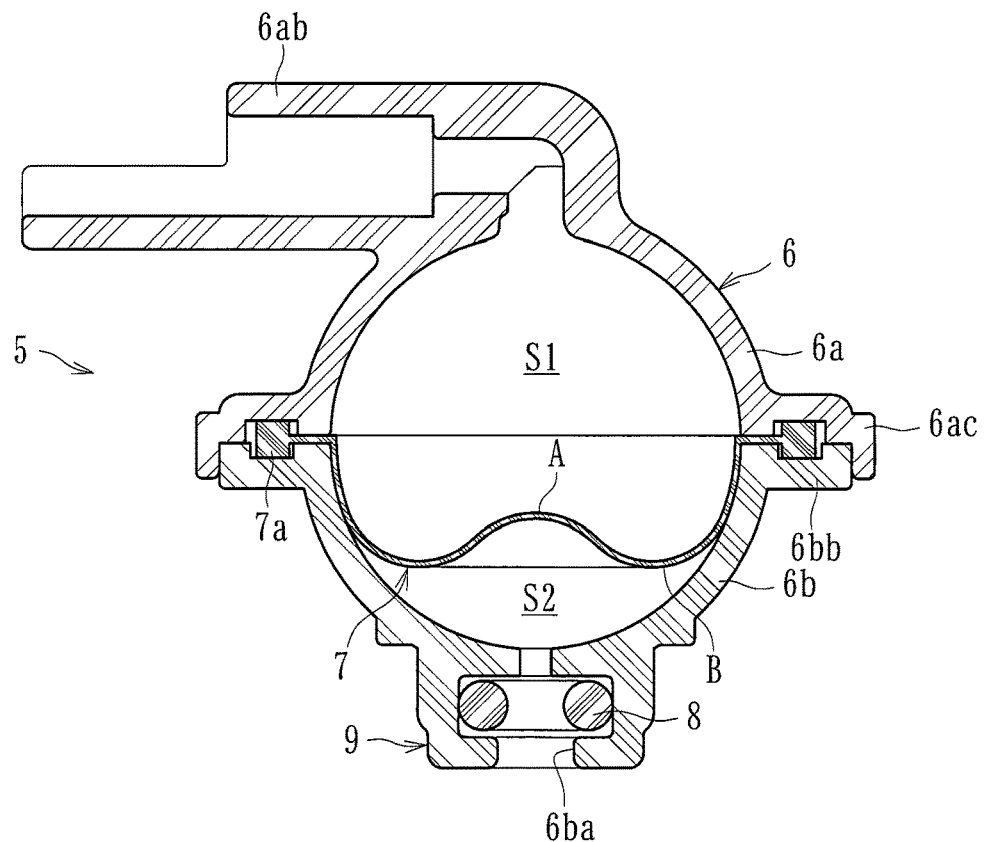
[Fig. 5]
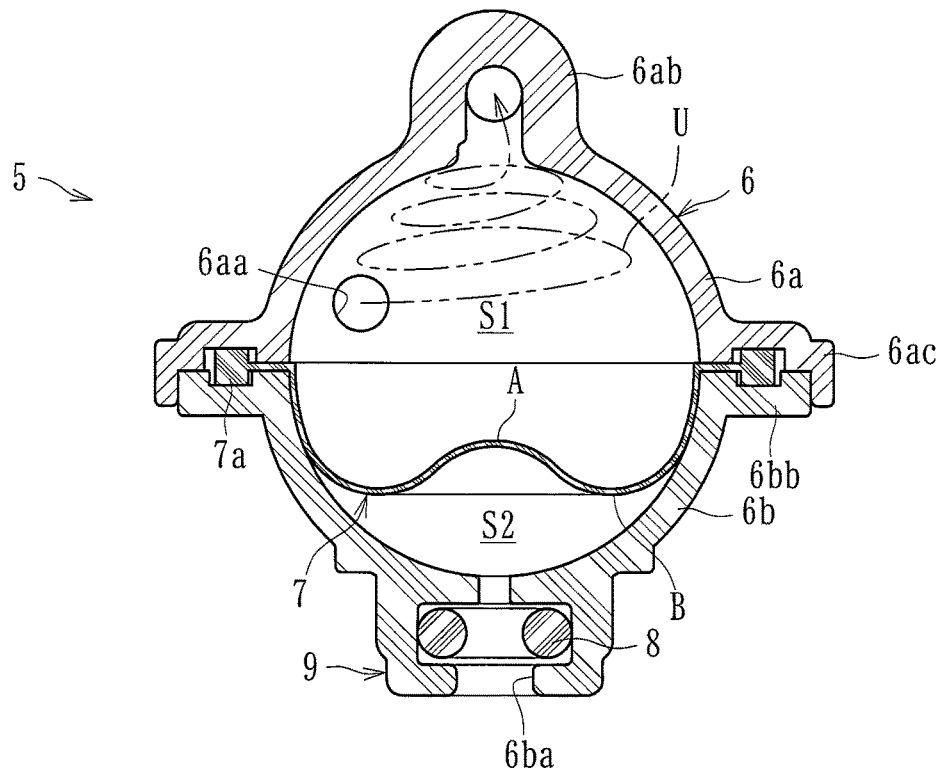

[Fig. 6]
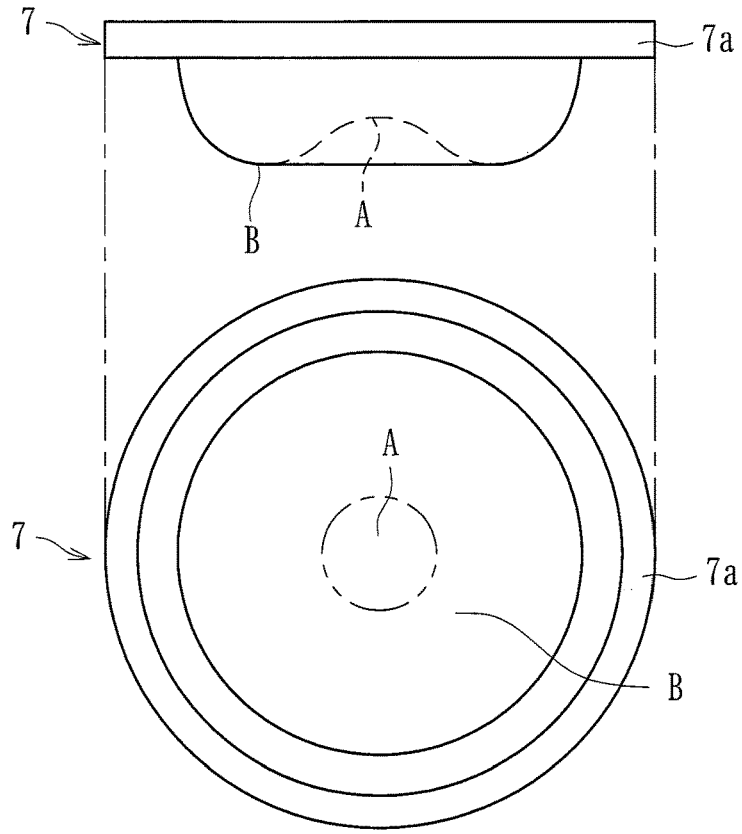
[Fig. 7]
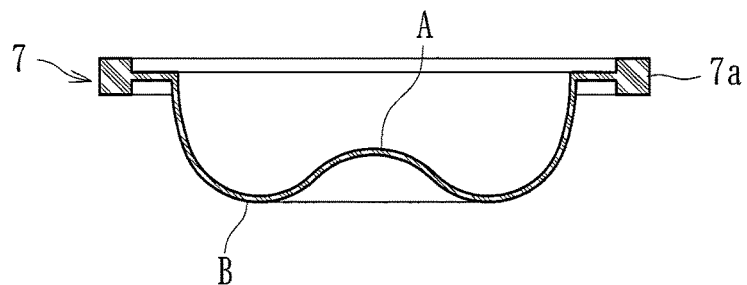
[Fig. 8]
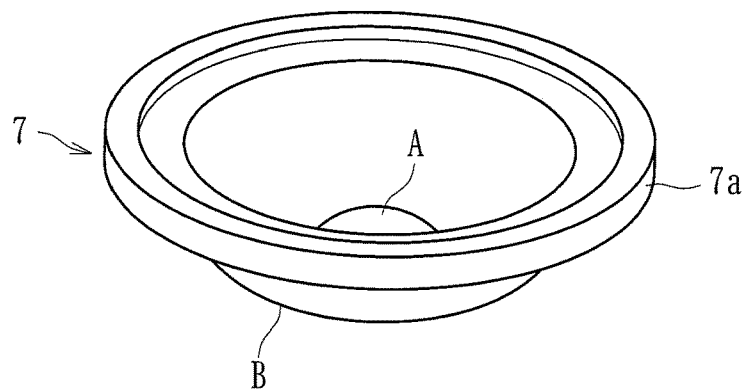

[Fig. 9]
(a)
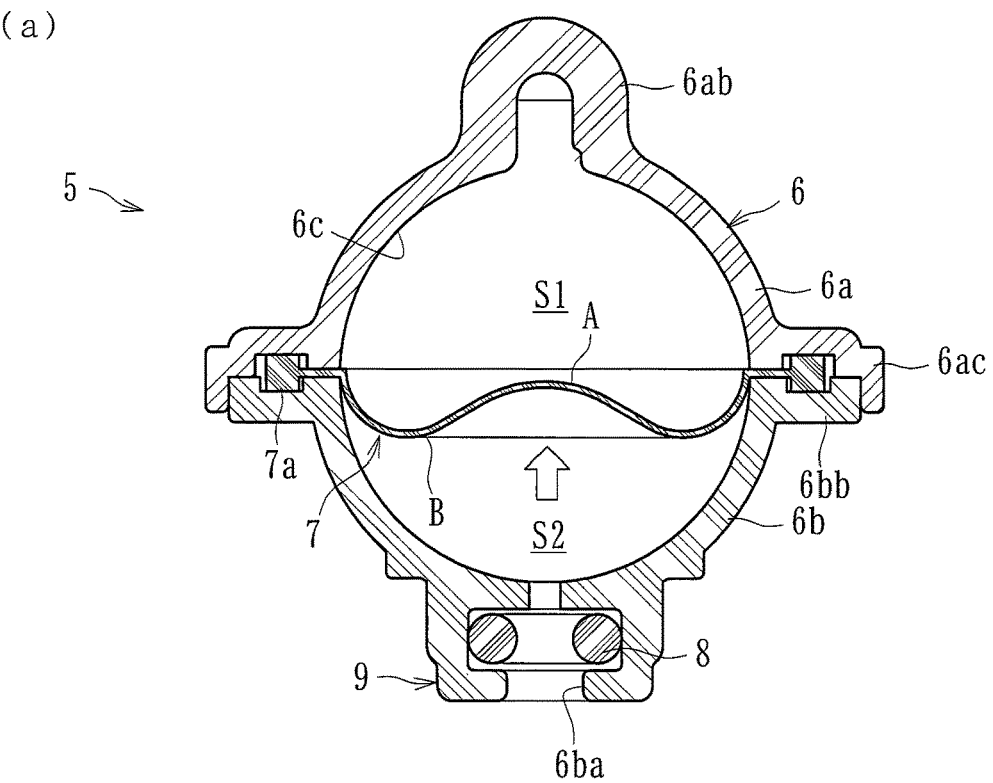
(b)
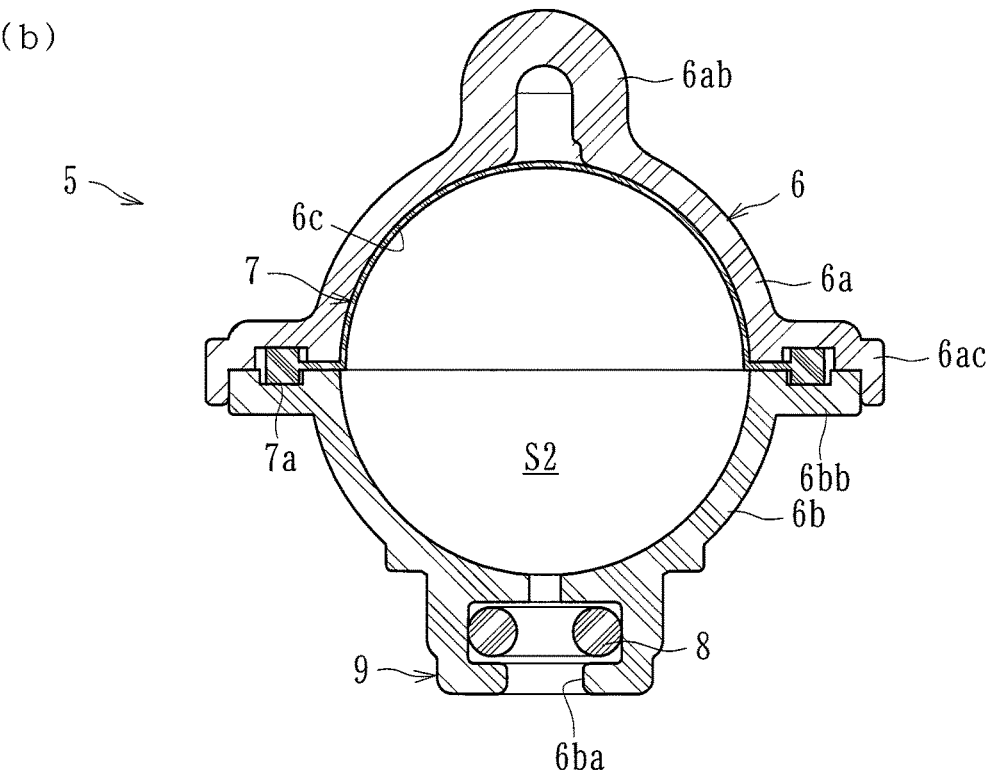

[ Fig. 10 ]
(a)
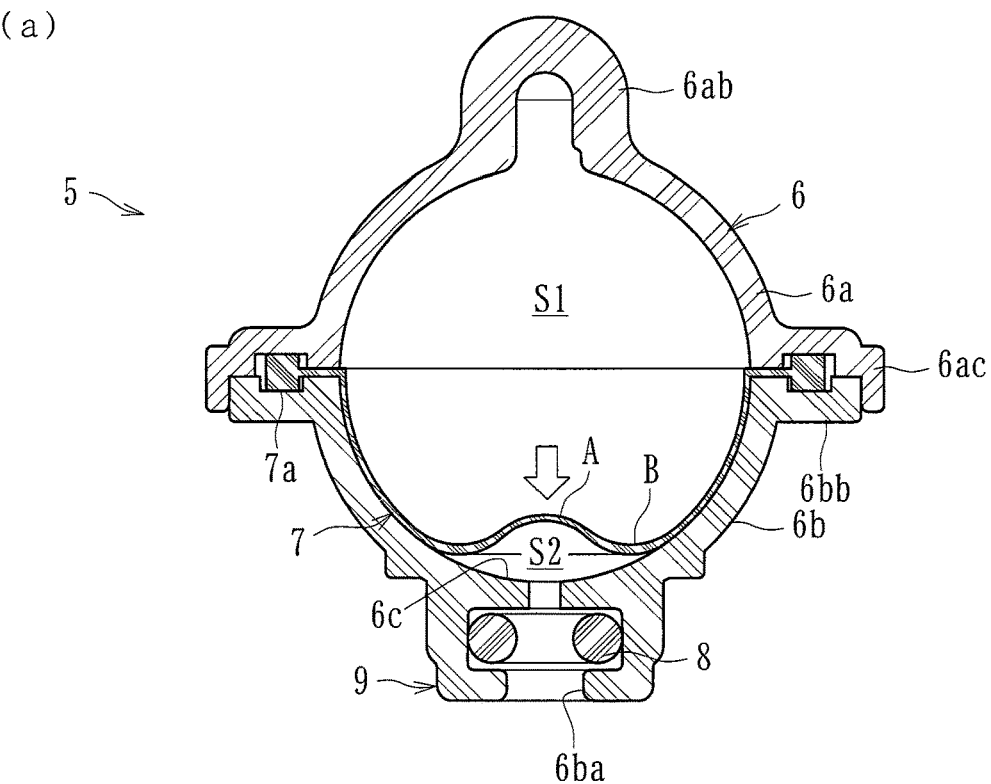
(b)
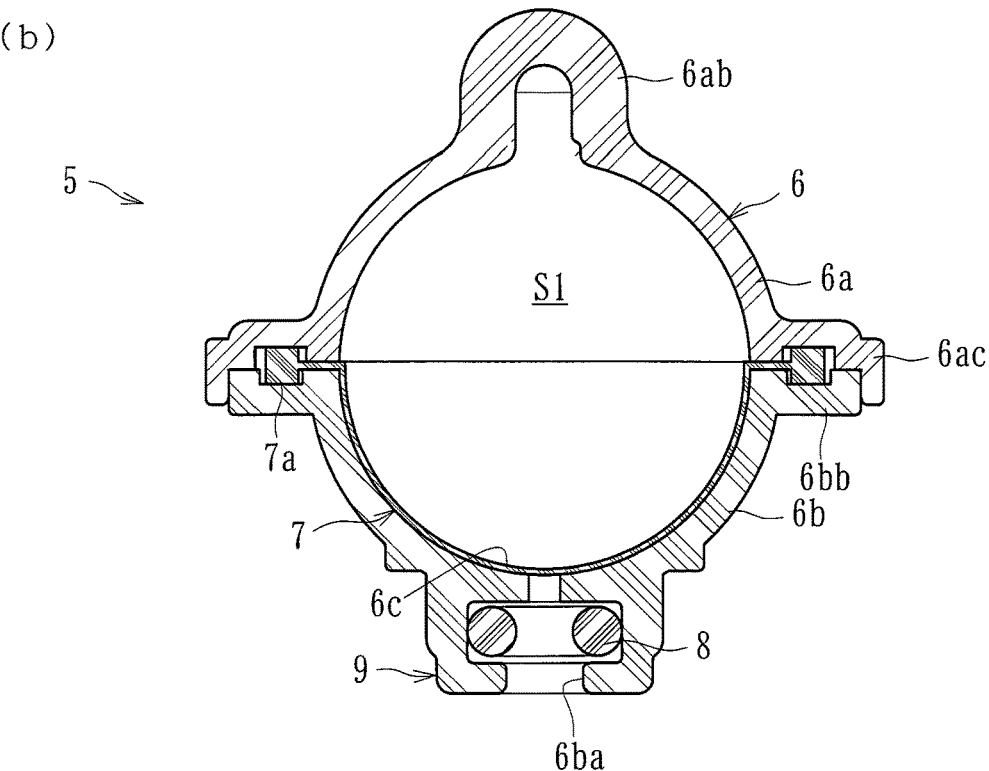

[Fig. 11]
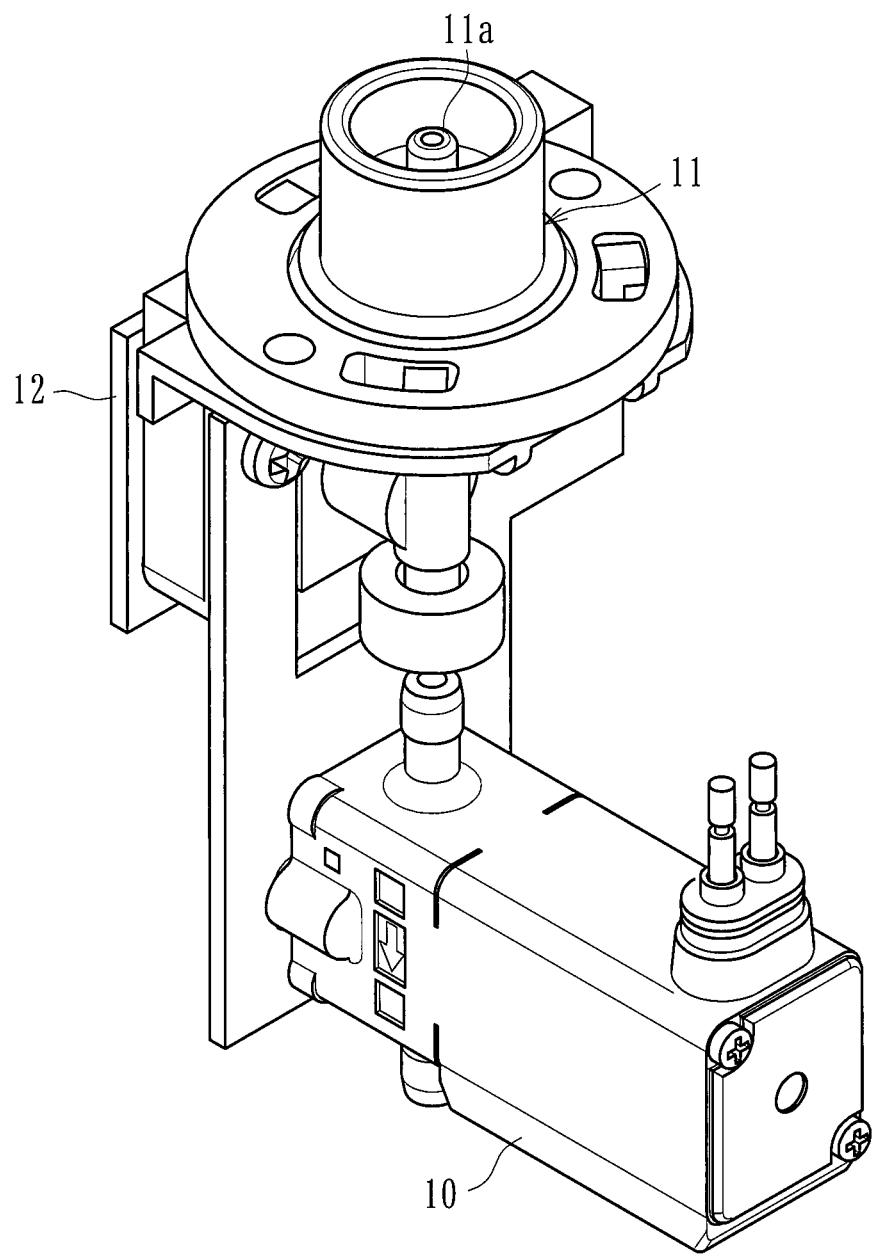

[Fig. 12]
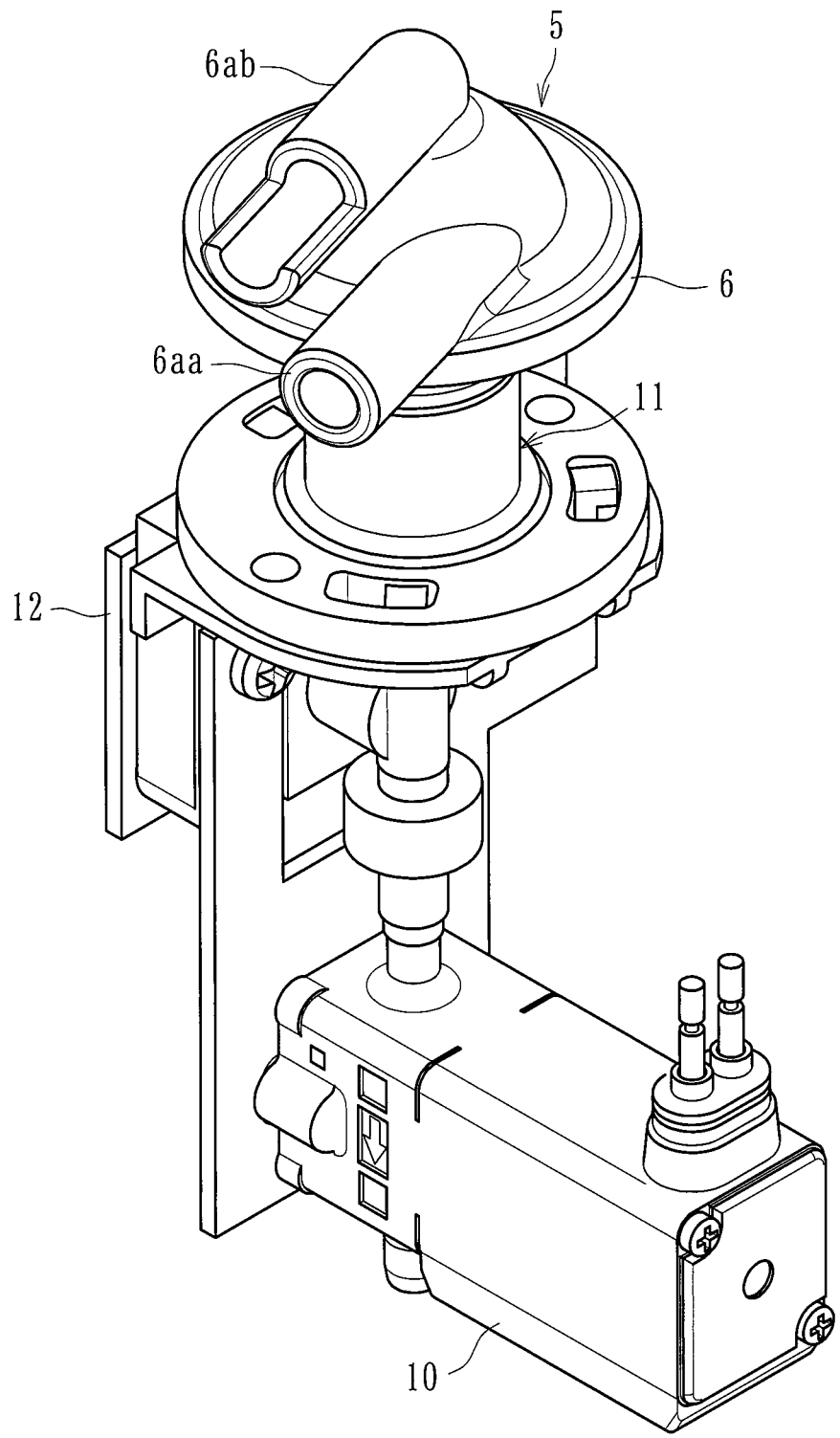

[Fig. 13]
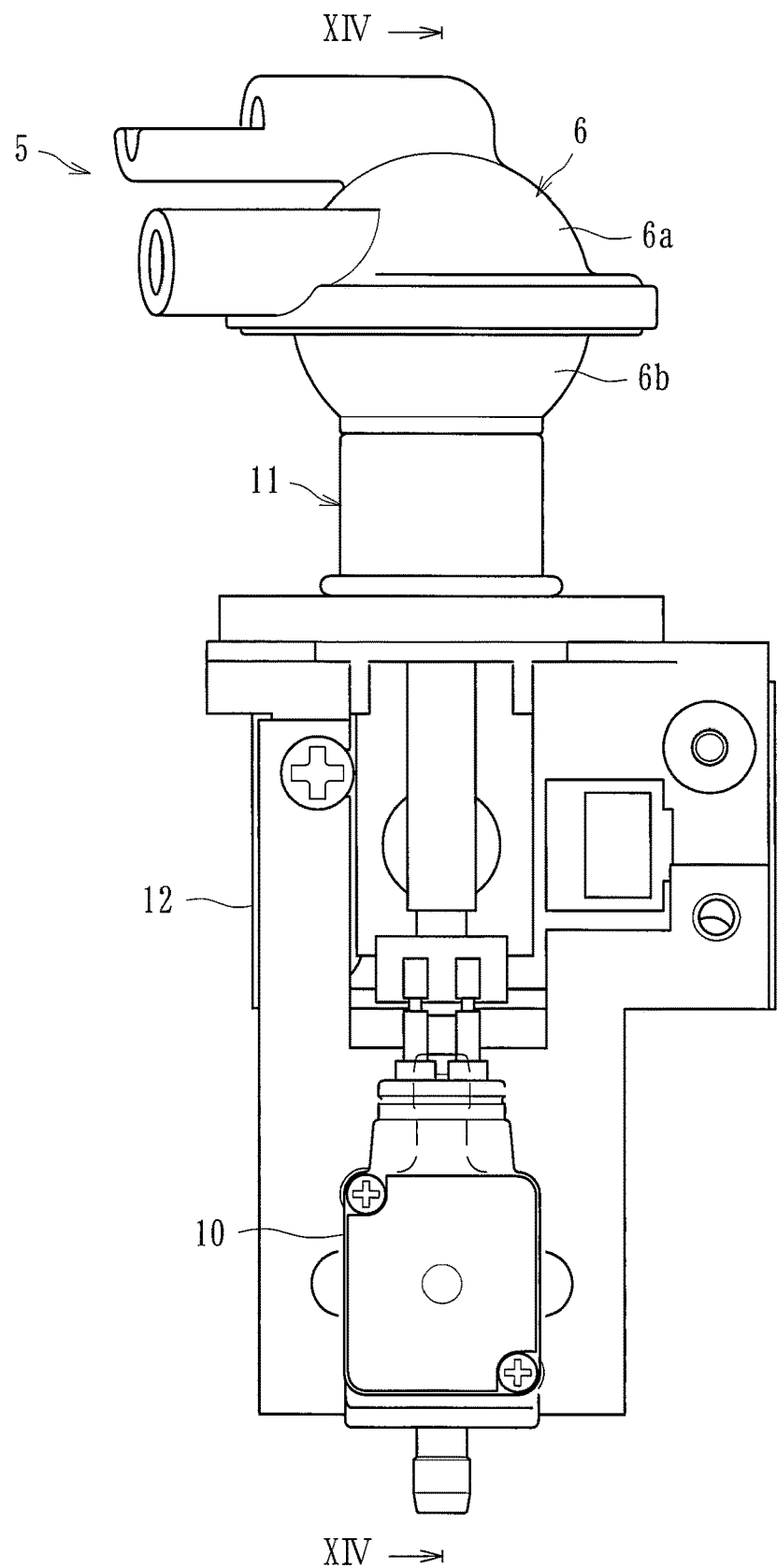

[Fig. 14]
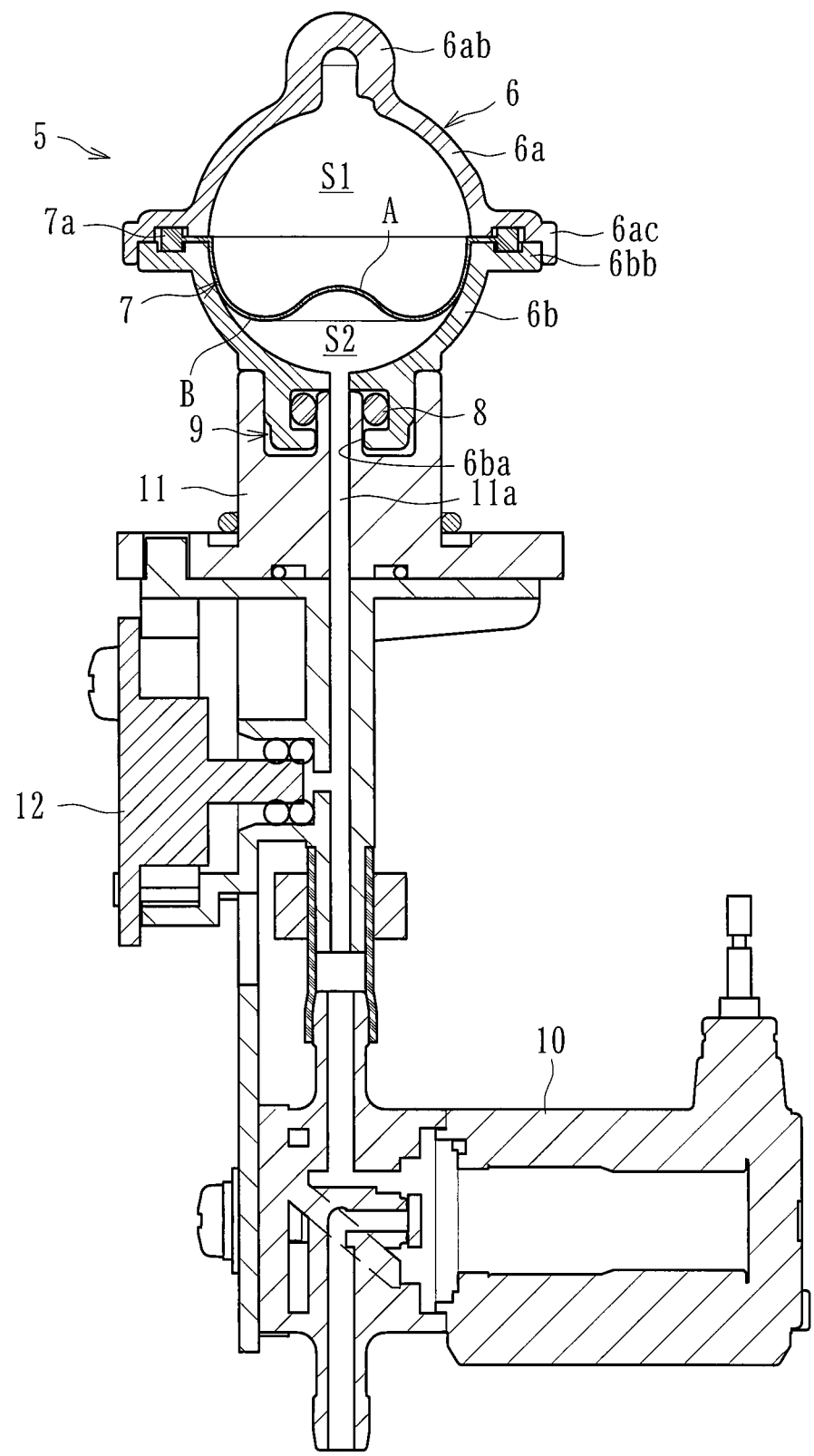

[ Fig. 15 ]
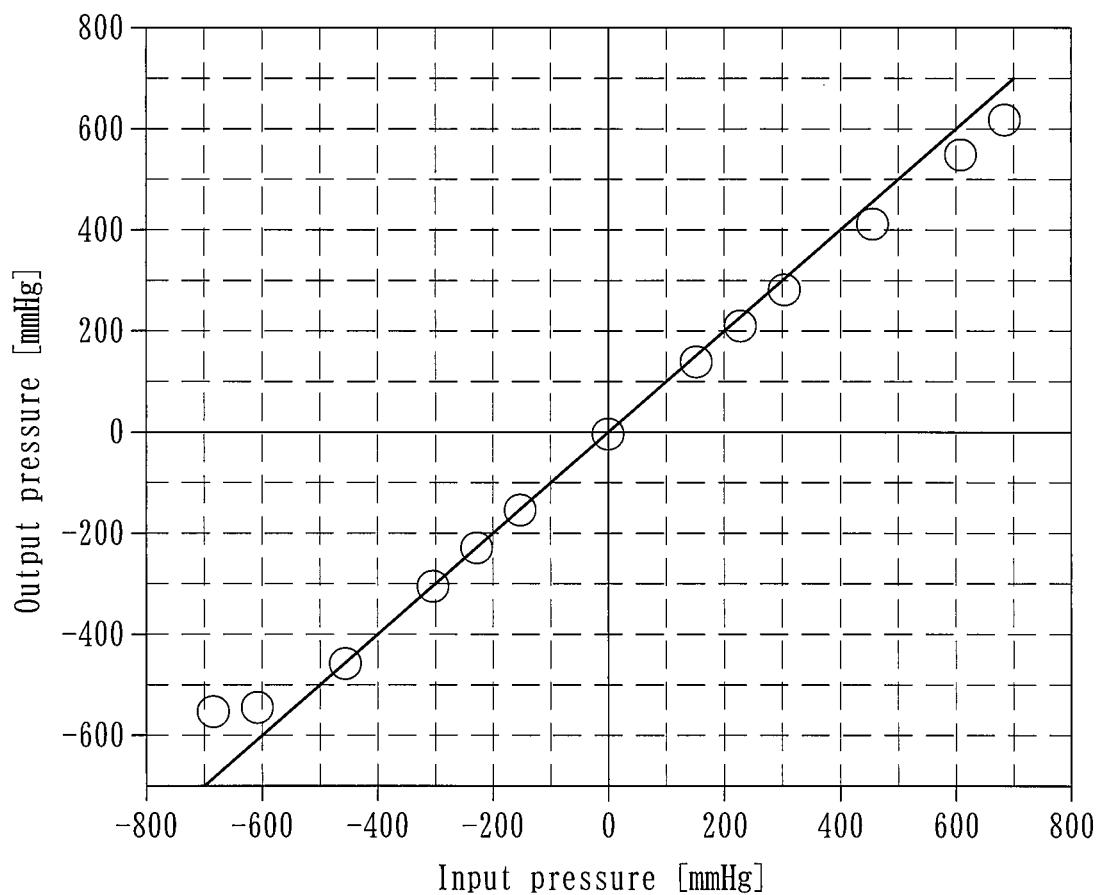

MEDICAL LIQUID-PRESSURE-DETECTING DEVICE

FIELD

The present teachings relate to a medical liquid-pressure-detecting device capable of detecting the pressure of liquid flowing in a flow route on the basis of pressure change in a gas chamber that occurs with the deformation of a diaphragm.

BACKGROUND

A typical blood circuit that is used in dialysis treatment as a blood purification treatment and through which the blood of a patient is extracorporeally circulated basically includes an arterial blood circuit to one end of which an arterial puncture needle is attached, and a venous blood circuit to one end of which a venous puncture needle is attached. A dialyzer serving as a blood purifier is connectable to the other respective ends of the arterial blood circuit and the venous blood circuit. The arterial blood circuit is provided with a peristaltic blood pump. When the blood pump is activated with the arterial puncture needle and the venous puncture needle being stuck in the patient, blood is collected through the arterial puncture needle. Furthermore, the collected blood is caused to flow through the arterial blood circuit and is introduced into the dialyzer, where the blood is purified. The purified blood is further caused to flow through the venous blood circuit and is returned into the body of the patient through the venous puncture needle. Thus, the dialysis treatment is performed.

The known blood circuit that performs the above extracorporeal circulation is provided with a medical liquid-pressure-detecting device for detecting the pressure of liquid such as blood (see PTL 1, for example). Such a known medical liquid-pressure-detecting device includes a diaphragm that is deformable in accordance with pressure change that occurs when a negative pressure or a positive pressure is generated in the liquid. The medical liquid-pressure-detecting device is capable of detecting the pressure of the liquid on the basis of the pressure change in a gas that occurs with the deformation of the diaphragm. The diaphragm has an arc shape that is concave either on the liquid side or on the gas side. If the arc shape projects on the gas side, a sensor for negative-pressure detection capable of detecting negative pressure is provided. If the arc shape projects on the liquid side, a sensor for positive-pressure detection capable of detecting positive pressure is provided.

PTL 1: U.S. Pat. No. 8,092,414 the teachings of which are incorporated by reference herein for all purposes.

SUMMARY

However, the above known medical liquid-pressure-detecting device needs to include a sensor dedicated to the detection of negative pressure and a sensor dedicated to the detection of positive pressure. Therefore, if the device is applied to a part where the liquid as the object of pressure detection can have both negative pressure and positive pressure, two sensors for negative pressure and positive pressure, respectively, need to be provided. Moreover, the sensor for negative pressure and the sensor for positive pressure differ from each other only in the direction of projection of the diaphragm and cannot be distinguished from each other by their appearance. Therefore, if an unintended one of the two is used accidentally, a defective product is provided.

The present teachings have been conceived in view of the above circumstances and provides a medical liquid-pressure-detecting device capable of detecting both the negative pressure and the positive pressure of liquid, whereby the misconnection of the device to a liquid flow route can be prevented.

According to the teachings herein, there is provided a medical liquid-pressure-detecting device including a chamber unit connected to a liquid flow route and having an inlet from which liquid flowing in the flow route is taken in and an outlet from which the liquid is discharged, the chamber unit being capable of storing the liquid by a predetermined amount while the liquid flows from the inlet to the outlet; and a diaphragm dividing an inside of the chamber unit into a liquid chamber that stores the liquid and a gas chamber that stores a predetermined gas, the diaphragm being deformable in accordance with a pressure of the liquid in the liquid chamber, the medical liquid-pressure-detecting device being capable of detecting a pressure of the liquid in the flow route on the basis of a change in the pressure in the gas chamber that is caused by the deformation of the diaphragm. The diaphragm includes a negative-pressure-detecting region that deforms toward one side when a negative pressure is generated in the liquid stored in the liquid chamber, and a positive-pressure-detecting region that deforms toward an other side when a positive pressure is generated in the liquid stored in the liquid chamber.

According to the teachings herein, in the medical liquid-pressure-detecting device taught herein, the positive-pressure-detecting region is a central region of the diaphragm that projects toward the liquid chamber, and the negative-pressure-detecting region is a region of the diaphragm that projects toward the gas chamber between a peripheral edge and the positive-pressure-detecting region.

According to the teachings herein, in the medical liquid-pressure-detecting device taught herein, the negative-pressure-detecting region and the positive-pressure-detecting region each form an arc shape projecting downward or an arc shape projecting upward and are gently continuous with each other.

According to the teachings herein, in the medical liquid-pressure-detecting device taught herein, the chamber unit has a spherical shape, and the negative-pressure-detecting region and the positive-pressure-detecting region come into close contact with an inner wall of the chamber unit when a negative pressure or a positive pressure that is greater than predetermined is generated in the liquid stored in the liquid chamber.

According to the teachings herein, in the medical liquid-pressure-detecting device taught herein, the negative-pressure-detecting region and the positive-pressure-detecting region have a substantially uniform thickness.

According to the teachings herein, in the medical liquid-pressure-detecting device taught herein, the outlet is provided at a top of the liquid chamber of the chamber unit and at a center position in a widthwise direction, and the inlet is provided at a position of the liquid chamber that is lower than the outlet and is shifted from a center position in the widthwise direction by a predetermined length.

According to the teachings herein, in the medical liquid-pressure-detecting device taught herein, the positive-pressure-detecting region is a region projecting upward at a center of the diaphragm and is positioned below a center of a swirl of the liquid that is generated when the liquid flows from the inlet to the outlet.

According to the teachings herein, in the medical liquid-pressure-detecting device taught herein, the chamber unit includes a connecting portion that is connectable to a sensor unit for detecting a change in a pressure of the gas stored in the gas chamber, and the connecting portion includes a sealing member that seals a connected portion of the sensor unit and into which the connected portion is fittable, and a communication hole into which the connected portion is insertable.

According to the teachings herein, there is provided a liquid flow route to which the medical liquid-pressure-detecting device taught herein is connected.

According to the teachings herein, there is provided a medical apparatus including the liquid flow route taught herein.

According to the teachings herein, the diaphragm includes the negative-pressure-detecting region that deforms toward one side when a negative pressure is generated in the liquid stored in the liquid chamber, and the positive-pressure-detecting region that deforms toward the other side when a positive pressure is generated in the liquid stored in the liquid chamber. Therefore, both the negative pressure and the positive pressure of the liquid are detectable. Hence, the misconnection of the device to the liquid flow route can be prevented.

According to the teachings herein, the positive-pressure-detecting region is the central region of the diaphragm that projects toward the liquid chamber, and the negative-pressure-detecting region is the region of the diaphragm that projects toward the gas chamber between the peripheral edge and the positive-pressure-detecting region. Therefore, the detection of negative pressure and the detection of positive pressure can be performed accurately and smoothly with a single diaphragm.

According to the teachings herein, the negative-pressure-detecting region and the positive-pressure-detecting region each form an arc shape projecting downward or an arc shape projecting upward and are gently continuous with each other. Therefore, smooth deformation of the diaphragm is realized both at the generation of a negative pressure and at the generation of a positive pressure. In addition, the stagnation of the liquid in the liquid chamber can be suppressed.

According to the teachings herein, the chamber unit has a spherical shape, and the negative-pressure-detecting region and the positive-pressure-detecting region come into close contact with the inner wall of the chamber unit when a negative pressure or a positive pressure that is greater than predetermined is generated in the liquid stored in the liquid chamber. Therefore, a negative pressure or a positive pressure that is smaller than predetermined can be detected accurately.

According to the teachings herein, the negative-pressure-detecting region and the positive-pressure-detecting region have a substantially uniform thickness. Therefore, even if the pressure of the liquid changes from a negative pressure to a positive pressure or from a positive pressure to a negative pressure, continuous pressure responsiveness can be obtained.

According to the teachings herein, the outlet is provided at the top of the liquid chamber of the chamber unit and at the center position in the widthwise direction, and the inlet is provided at the position of the liquid chamber that is lower than the outlet and is shifted from the center position in the widthwise direction by a predetermined length. Therefore, the liquid introduced from the inlet flows upward while forming a swirl in the chamber unit and is discharged from the outlet. Thus, the stagnation of bubbles or the like contained in the liquid in the chamber unit can be suppressed.

According to the teachings herein, the positive-pressure-detecting region is the region projecting upward at the center of the diaphragm and is positioned below the center of the swirl of the liquid that is generated when the liquid flows from the inlet to the outlet. Since the positive-pressure-detecting region can be positioned below the center of the swirl where the liquid tends to stagnate when the swirl is generated in the chamber unit, the stagnation of the liquid in the chamber unit can be suppressed. Hence, the positive-pressure-detecting region can exert both a function of detecting positive pressure by deforming in accordance with the positive pressure and a function of suppressing the stagnation of the liquid in the liquid chamber.

According to the teachings herein, the chamber unit includes the connecting portion that is connectable to the sensor unit for detecting the change in the pressure of the gas stored in the gas chamber, and the connecting portion includes the sealing member that seals the connected portion of the sensor unit and into which the connected portion is fittable, and the communication hole into which the connected portion is insertable. Therefore, the chamber unit and the sensor unit can be connected to each other easily and assuredly.

According to the teachings herein, the advantageous effects produced by the teachings herein can be imparted to the liquid flow route.

According to the teachings herein, the advantageous effects produced by the teachings herein can be imparted to the medical apparatus.

BRIEF DESCRIPTION OF THE DRAWINGS

FIG. 1 is a schematic diagram illustrating liquid flow routes (an extracorporeal-circulation circuit or the like) and a blood purification apparatus to which a medical liquid-pressure-detecting device according to an embodiment of the present teachings are applied.

FIG. 2 is a perspective view of the medical liquid-pressure-detecting device.

FIG. 3 is a third-angle projection of the medical liquid-pressure-detecting device.

FIG. 4 is a sectional view taken along line IV-IV illustrated in FIG. 3.

FIG. 5 is a sectional view taken along line V-V illustrated in FIG. 3.

FIG. 6 includes a front view and a plan view of a diaphragm included in the medical liquid-pressure-detecting device.

FIG. 7 is a vertical sectional view of the diaphragm.

FIG. 8 is a perspective view of the diaphragm.

FIG. 9 includes sectional views of the medical liquid-pressure-detecting device and illustrate how the diaphragm deforms under negative pressure: part (a) illustrates a state where the deformation is in progress, and part (b) illustrates a state where a negative pressure greater than predetermined is generated.

FIG. 10 includes sectional views of the medical liquid-pressure-detecting device and illustrate how the diaphragm deforms under positive pressure: part (a) illustrates a state where the deformation is in progress, and part (b) illustrates a state where a positive pressure greater than predetermined is generated.

FIG. 11 is a perspective view of a sensor unit connectable to a chamber unit of the medical liquid-pressure-detecting device (with the chamber unit yet to be connected).

FIG. 12 is a perspective view of the sensor unit connectable to the chamber unit of the medical liquid-pressure-detecting device (with the chamber unit connected).

FIG. 13 is a front view of the medical liquid-pressure-detecting device with the sensor unit connected.

FIG. 14 is a sectional view taken along line XIV-XIV illustrated in FIG. 13.

FIG. 15 is a graph illustrating the pressure responsiveness of the medical liquid-pressure-detecting device.

DETAILED DESCRIPTION

An embodiment of the present teachings are described specifically with reference to the drawings.

A medical liquid-pressure-detecting device according to an embodiment is capable of detecting the pressure of liquid flowing in a flow route and is applied to a blood purification apparatus illustrated in FIG. 1. As illustrated in FIG. 1, the blood purification apparatus is applied to a dialysis apparatus for purifying the blood of a patient while extracorporeally circulating the blood and includes a blood circuit 1, a dialyzer 2 serving as a blood purifier, and air-trap chambers 4.

The dialyzer 2 includes a housing that houses a plurality of hollow fibers each having very small holes (pores). The housing has a blood introduction port 2a, a blood delivery port 2b, a dialysate introduction port 2c, and a dialysate delivery port 2d. The blood circuit 1 is formed of flexible tubes and includes an arterial blood circuit 1a to a distal end of which an arterial puncture needle is connectable, and a venous blood circuit 1b to a distal end of which a venous puncture needle is connectable. A proximal end of the arterial blood circuit 1a is connected to the blood introduction port 2a of the dialyzer 2. A proximal end of the venous blood circuit 1b is connected to the blood delivery port 2b of the dialyzer 2.

Furthermore, a dialysate introduction tube L1 through which dialysate is introduced into the dialyzer 2 and a dialysate delivery tube L2 through which the dialysate (drain liquid) is delivered from the dialyzer 2 are attachable to the dialysis apparatus. A distal end of the dialysate introduction tube L1 is connected to the dialysate introduction port 2c of the dialyzer 2. A distal end of the dialysate delivery tube L2 is connected to the dialysate delivery port 2d of the dialyzer 2. In the present embodiment, a substitution-fluid introduction tube L3 that connects the dialysate introduction tube L1 and the venous blood circuit 1b to each other is provided. The arterial blood circuit 1a and the venous blood circuit 1b that form the blood circuit 1 (an extracorporeal circulation circuit), the dialysate introduction tube L1, the dialysate delivery tube L2, and the substitution-fluid introduction tube L3 are each made of a flexible tube that allows liquid to flow therethrough. The arterial blood circuit 1a and the venous blood circuit 1b are provided with the air-trap chambers 4, respectively, whereby bubbles contained in the liquid flowing in the blood circuit 1 can be removed.

The arterial blood circuit 1a is further provided with a blood pump P1 at a halfway position thereof. The blood pump P1 is a peristaltic pump that includes a rotor that rotates along the inner peripheral surface of a stator, and a pair of rollers provided to the rotor, and in which the rotor rotates in the direction of the flow of the liquid, and a squeezable flexible tube D1 connected to the arterial blood circuit 1a is squeezed by the pair of rollers, whereby the liquid can be delivered.

Another squeezable flexible tube D2 is connected to a halfway position of the dialysate introduction tube L1. Yet another squeezable flexible tube D3 is connected to a halfway position of the substitution-fluid introduction tube L3. The squeezable flexible tube D2 and the squeezable flexible tube D3 are attached to peristaltic pumps P2 and P3, respectively, included in the dialysis apparatus. Yet another squeezable flexible tube D4 is connected to a halfway position of the dialysate delivery tube L2 and is attached to a peristaltic pump P4 included in the dialysis apparatus. When the peristaltic pump P4 is activated, drain liquid can be discharged to the outside of the circuit.

As with the blood pump P1, the peristaltic pumps P2 to P4 each include, a rotor that rotates along the inner peripheral surface of a stator, and a pair of rollers provided to the rotor. The rotor rotates in the direction of the flow of the liquid, and a corresponding one of the squeezable flexible tubes (D2 to D4) connected to a corresponding one of the flow routes is squeezed by the pair of rollers, whereby the liquid can be delivered. When the blood pump P1 (a blood pump) is activated with the arterial puncture needle and the venous puncture needle being stuck in the patient, the blood of the patient is allowed to extracorporeally circulate through the arterial blood circuit 1a and the venous blood circuit 1b.

On the other hand, the proximal end of the dialysate introduction tube L1 is connected to a storage bag B1 that stores dialysate to be supplied to the dialyzer 2. The dialysate introduction tube L1 is provided at a halfway position thereof with a heating bag or the like (not illustrated) for heating the dialysate. When the peristaltic pump P2 is activated, the dialysate in the storage bag B1 flows toward the dialyzer 2 while the dialysate (drain liquid) in the dialyzer 2 flows through the dialysate delivery tube L2 and is discharged to the outside. The storage bag B1 is hooked on a hook F provided to the dialysis apparatus, whereby the storage bag B1 is weighed by a weighing machine 3 in real time. Thus, the dialysate can be supplied to the dialyzer 2 at a preset flow rate while being discharged from the dialyzer 2.

In the present embodiment, the squeezable flexible tube D3 is connected to the substitution-fluid introduction tube L3 that branches off from the dialysate introduction tube L1, and the squeezable flexible tube D3 is attached to the peristaltic pump P3. When the peristaltic pumps P2 and P3 are activated, the dialysate in the storage bag B1 can be supplied to the venous blood circuit 1b, whereby substitution can be performed. In the present embodiment, the venous blood circuit 1b is provided with one of the air-trap chambers 4, and the air-trap chamber 4 is connected to the distal end of the substitution-fluid introduction tube L3, whereby the dialysate can be supplied. Alternatively, the distal end of the substitution-fluid introduction tube L3 may be connected to the air-trap chamber 4 connected to the arterial blood circuit 1a, whereby the dialysate may be supplied. Note that the distal end of the substitution-fluid introduction tube L3 may be connected to an element other than the air-trap chambers 4.

In the present embodiment, a medical liquid-pressure-detecting device 5 is provided at each of positions of the arterial blood circuit 1a (a liquid flow route) that are on the upstream side (a position between the distal end of the arterial blood circuit 1a and the blood pump P1) and the downstream side (a position between the blood pump P1 and the dialyzer 2), respectively, of the blood pump P1, and a position of the dialysate delivery tube L2 (a liquid flow route) that is between the dialyzer 2 and the peristaltic pump P4.

As illustrated in FIGS. 2 to 8, the medical liquid-pressure-detecting device 5 according to the present embodiment includes a chamber unit 6 connected to a liquid flow route (in the present embodiment, each of the arterial blood circuit 1a and the dialysate delivery tube L2) and having an inlet 6aa from which the liquid flowing in the flow route is taken in and an outlet 6ab from which the liquid is discharged, the chamber unit 6 being capable of storing the liquid by a predetermined amount while the liquid flows from the inlet 6aa to the outlet 6ab; and a diaphragm 7 dividing the inside of the chamber unit 6 into a liquid chamber S1 that stores the liquid and a gas chamber S2 that stores a predetermined gas (specifically, air), the diaphragm 7 being deformable in accordance with the pressure of the liquid in the liquid chamber S1.

The chamber unit 6 is an assembly including an upper case 6a having the inlet 6aa and the outlet 6ab, and a lower case 6b having a connecting portion 9 that is connectable to a sensor unit (see FIG. 11) for detecting the change in the gas pressure in the gas chamber S2. The chamber unit 6 generally has a spherical shape. The upper case 6a has a flange portion 6ac at the bottom thereof. The lower case 6b has a flange portion 6bb at the top thereof. The flange portions 6ac and 6bb hold a peripheral edge 7a of the diaphragm 7 therebetween.

The diaphragm 7 includes a negative-pressure-detecting region B that deforms toward one side (in the present embodiment, upward in the drawings and in a direction of an arrow illustrated in FIG. 9(a)) when a negative pressure is generated in the liquid stored in the liquid chamber S1, and a positive-pressure-detecting region A that deforms toward the other side (in the present embodiment, downward in the drawings and in a direction of an arrow illustrated in FIG. 10(a)) when a positive pressure is generated in the liquid stored in the liquid chamber S1. More specifically, the positive-pressure-detecting region A is a central region of the diaphragm 7 that projects toward the liquid chamber S1, and the negative-pressure-detecting region B is a region of the diaphragm 7 that projects toward the gas chamber S2 between the peripheral edge 7a and the positive-pressure-detecting region A.

In particular, the negative-pressure-detecting region B according to the present embodiment forms an arc shape projecting downward (parabolically convex downward) between the peripheral edge 7a of the diaphragm 7 and the positive-pressure-detecting region A, whereas the positive-pressure-detecting region A forms an arc shape projecting upward (parabolically convex upward) at the center of the diaphragm 7. The positive-pressure-detecting region A and the negative-pressure-detecting region B are gently continuous with each other from the center toward the peripheral edge 7a of the diaphragm 7.

In the present embodiment, when a negative pressure or a positive pressure that is greater than predetermined is generated in the liquid stored in the liquid chamber S1, the negative-pressure-detecting region B and the positive-pressure-detecting region A can come into close contact with an inner wall 6c of the chamber unit 6. That is, when a negative pressure is generated in the liquid stored in the liquid chamber S1, the negative-pressure-detecting region B of the diaphragm 7 deforms upward in accordance with the pressure as illustrated in FIG. 9(a). Then, when the negative pressure reaches a level greater than predetermined, the negative-pressure-detecting region B and the positive-pressure-detecting region A come into close contact with the inner wall 6c of the upper case 6a of the chamber unit 6 as illustrated in FIG. 9(b). On the other hand, when a positive pressure is generated in the liquid stored in the liquid chamber S1, the positive-pressure-detecting region A of the diaphragm 7 deforms downward in accordance with the pressure as illustrated in FIG. 10(a). Then, when the positive pressure reaches a level greater than predetermined, the negative-pressure-detecting region B and the positive-pressure-detecting region A come into close contact with the inner wall 6c of the lower case 6b of the chamber unit 6 as illustrated in FIG. 10(b).

As illustrated in FIGS. 11 to 14, the connecting portion 9 is a region that is connectable to a sensor unit 10 for detecting the pressure change in the gas stored in the gas chamber S2 of the chamber unit 6. The connecting portion 9 includes a sealing member 8 (specifically, an O ring) that seals a connected portion 11a of the sensor unit 10 and into which the connected portion 11a is fittable, and a communication hole 6ba into which the connected portion 11a is insertable. That is, when the sensor unit 10 is connected to the chamber unit 6, the sensor unit 10 communicates with the gas chamber S2 of the chamber unit 6 through the connected portion 11a as illustrated in FIG. 14, thereby becoming capable of detecting the change in the pressure of the gas stored in the gas chamber S2. Thus, the pressure of the liquid that flows in the flow route can be detected on the basis of the pressure change in the gas chamber S2 that is caused by the deformation of the diaphragm 7 (the negative-pressure-detecting region B and the positive-pressure-detecting region A).

As described above, when the connected portion 11a is inserted and fitted into the communication hole 6ba, the chamber unit 6 and the sensor unit 10 can be connected to each other while the connected portion 11a is sealed by the sealing member 8. In the drawings, reference numeral 12 denotes a stay for securing the sensor unit 10 and the connected portion 11a at predetermined positions of the blood purification apparatus, and reference numeral 11 denotes a wall portion that covers and protects the outer periphery of the connected portion 11a.

Hence, the diaphragm 7 is preferably made of a soft, highly air-permeable member, such as silicon, SEBS, isoprene, or the like. Furthermore, the positive-pressure-detecting region A and the negative-pressure-detecting region B are generally formed with a substantially uniform thickness. That is, since the positive-pressure-detecting region A and the negative-pressure-detecting region B generally have a substantially uniform thickness, straight and continuous pressure linearity as graphed in FIG. 15 can be provided in a transition from the negative pressure to the positive pressure or from the positive pressure to the negative pressure without being affected by the elasticity of the diaphragm 7.

On the other hand, the outlet 6ab is provided at the top of the liquid chamber S1 of the chamber unit 6 and at the center position in the widthwise direction (the lateral direction in FIG. 5). The inlet 6aa is provided at a position of the liquid chamber S1 that is lower than the outlet 6ab and is shifted from the center position in the widthwise direction by a predetermined length (t) (shifted leftward in FIG. 5 by a predetermined length). Since the inlet 6aa is offset from the center of the chamber unit 6 in the widthwise direction by a predetermined length (t), the liquid introduced from the inlet 6aa flows upward while forming a swirl (denoted by reference character U in FIGS. 3 and 5) in the chamber unit 6 and is discharged from the outlet 6ab. Thus, the stagnation of bubbles or the like contained in the liquid in the chamber unit 6 can be suppressed.

Furthermore, the positive-pressure-detecting region A is a region projecting upward at the center of the diaphragm 7 and is positioned below the center of the swirl of the liquid that is generated when the liquid flows from the inlet 6aa to the outlet 6ab. Since the positive-pressure-detecting region A can be positioned below the center of the swirl (denoted by reference character U in FIGS. 3 and 5) where the liquid tends to stagnate when the swirl is generated in the chamber unit 6, the stagnation of the liquid in the chamber unit 6 can be suppressed. Hence, the positive-pressure-detecting region A can exert both a function of detecting positive pressure by deforming in accordance with the positive pressure and a function of suppressing the stagnation of the liquid in the liquid chamber S1.

According to the above embodiment, the diaphragm 7 includes the negative-pressure-detecting region B that deforms toward one side when a negative pressure is generated in the liquid stored in the liquid chamber S1, and the positive-pressure-detecting region A that deforms toward the other side when a positive pressure is generated in the liquid stored in the liquid chamber S1. Therefore, both the negative pressure and the positive pressure of the liquid are detectable. Hence, the misconnection of the device to the liquid flow route can be prevented. In particular, according to the present embodiment, the positive-pressure-detecting region A is a central region of the diaphragm 7 that projects toward the liquid chamber S1, and the negative-pressure-detecting region B is a region of the diaphragm 7 that projects toward the gas chamber S2 between the peripheral edge 7a and the positive-pressure-detecting region A. Therefore, the detection of negative pressure and the detection of positive pressure can be performed accurately and smoothly with a single diaphragm 7.

Furthermore, the negative-pressure-detecting region B and the positive-pressure-detecting region A form arc shapes projecting downward and upward, respectively, and are gently continuous with each other. Therefore, smooth deformation of the negative-pressure-detecting region B and the positive-pressure-detecting region A is realized. Accordingly, smooth deformation of the diaphragm 7 is realized both at the generation of a negative pressure and at the generation of a positive pressure. In addition, since the liquid chamber S1 has no steps or the like, the stagnation of the liquid in the liquid chamber S1 can be suppressed.

Furthermore, according to the present embodiment, the chamber unit 6 has a spherical shape, and the negative-pressure-detecting region B and the positive-pressure-detecting region A can come into close contact with the inner wall 6c of the chamber unit 6 when a negative pressure or a positive pressure that is greater than predetermined is generated in the liquid stored in the liquid chamber S1. Therefore, a negative pressure or a positive pressure that is smaller than predetermined can be detected more accurately than in a case where the diaphragm includes a region that comes into close contact with the inner wall 6c of the chamber unit 6 and a region that does not come into close contact with the inner wall 6c when a negative pressure or a positive pressure that is greater than predetermined is generated in the liquid stored in the liquid chamber S1.

Furthermore, according to the present embodiment, the negative-pressure-detecting region B and the positive-pressure-detecting region A have a substantially uniform thickness. Therefore, straight and continuous pressure linearity as illustrated in FIG. 15 is realized. Moreover, even if the pressure of the liquid changes from a negative pressure to a positive pressure or from a positive pressure to a negative pressure, continuous pressure responsiveness can be obtained. Note that the diaphragm 7 may be made of any of various material, as long as desired characteristics are obtained.

The chamber unit 6 according to the present embodiment includes the connecting portion 9 that is connectable to the sensor unit 10 for detecting the change in the pressure of the gas in the gas chamber S2. Furthermore, the connecting portion 9 includes the sealing member 8 that seals the connected portion 11a of the sensor unit 10 and into which the connected portion 11a is fittable, and the communication hole 6ba into which the connected portion 11a is insertable. Therefore, the chamber unit 6 and the sensor unit 10 can be connected to each other easily and assuredly.

In addition, the medical liquid-pressure-detecting device 5 according to the present embodiment is connected to the blood circuit 1 (in the present embodiment, the arterial blood circuit 1a). Therefore, the above advantageous effects can be imparted to the blood circuit 1 (a liquid flow route) and to a medical apparatus (a blood purification apparatus). The blood circuit 1 that is applicable is not limited to a blood circuit for dialysis and may be any extracorporeal-circulation circuit including circuits for another treatment. The medical liquid-pressure-detecting device 5 may be connected to the venous blood circuit 1b, another liquid flow route (such as a line for infusing a physiological saline solution) connected to the blood circuit 1, or a liquid flow route through which another liquid such as dialysate or a substitution fluid flows, instead of or as well as the arterial blood circuit 1a.

While an embodiment has been described above, the present teachings are not limited to the above embodiment. For example, the chamber unit 6 may be oriented upside down (that is, the chamber unit 6 may be oriented such that the liquid chamber S1 is provided on the lower side and the gas chamber S2 is provided on the upper side) to be connected to the liquid flow route. In addition, while the chamber unit 6 according to the above embodiment has a spherical shape, the chamber unit 6 may have another shape (a combination of upper and lower dome-shaped members, a combination of upper and lower arc-shaped members, or the like). Moreover, while the negative-pressure-detecting region B and the positive-pressure-detecting region A according to the above embodiment each project in an arc shape, the negative-pressure-detecting region B and the positive-pressure-detecting region A may each project in another shape (such as a triangular shape, or a projection with irregularities at the top thereof), or in an arc shape with a plurality of projections, or the like.

Furthermore, the dialyzer 2 may be replaced with another blood purifier (a hemofilter, a plasmapheresis device, a hemoperfusion device, or the like). Moreover, the blood circuit 1 may be replaced with another extracorporeal-circulation circuit (a mechanical heart and lung or the like) or a blood flow route that is not intended for extracorporeal circulation (such as a flow route for blood transfusion or the like). Furthermore, the blood purification treatment that is applicable is not limited to dialysis treatment, and the blood purification apparatus may be intended for another treatment for purifying the blood of a patient while extracorporeally circulating the blood.

The medical liquid-pressure-detecting device may have other additional functions or the like, as long as the device includes a diaphragm including a negative-pressure-detecting region that deforms toward one side when a negative pressure is generated in liquid stored in a liquid chamber and a positive-pressure-detecting region that deforms toward the other side when a positive pressure is generated in the liquid stored in the liquid chamber.

REFERENCE SIGN LIST 1 blood circuit
1a arterial blood circuit (flow route)
1b venous blood circuit (flow route)
2 dialyzer (blood purifier)
3 weighing machine
4 air-trap chamber
5 medical liquid-pressure-detecting device
6 chamber unit
6aa inlet
6ab outlet
6ba communication hole
6c inner wall
7 diaphragm
8 sealing member
9 connecting portion
10 sensor unit
A positive-pressure-detecting region
B negative-pressure-detecting region

The invention claimed is:

1. A medical liquid-pressure-detecting device comprising:
a chamber unit connected to a liquid flow route and having:
an inlet from which liquid flowing in the flow route is taken in and
an outlet from which the liquid is discharged, the chamber unit being capable of storing the liquid by a predetermined amount while the liquid flows from the inlet to the outlet; and
a diaphragm dividing an inside of the chamber unit into a liquid chamber that stores the liquid and a gas chamber that stores a predetermined gas, the diaphragm being deformable in accordance with a pressure of the liquid in the liquid chamber,
the medical liquid-pressure-detecting device being capable of detecting a pressure of the liquid in the flow route on a basis of a change in the pressure in the gas chamber that is caused by the deformation of the diaphragm,
wherein the diaphragm includes:
a negative-pressure-detecting region that deforms toward one side when a negative pressure is generated in the liquid stored in the liquid chamber, and
a positive-pressure-detecting region that has a region projecting upward at a center of the diaphragm and is positioned below a center of a swirl of the liquid that is generated when the liquid flows from the inlet to the outlet and the positive-pressure-detecting region deforms toward an other side when a positive pressure is generated in the liquid stored in the liquid chamber; and
wherein the outlet is provided at a top of the liquid chamber of the chamber unit and at a center position in a widthwise direction, and the inlet is provided at a position of the liquid chamber that is lower than the outlet is shifted from a center position in the widthwise direction by a predetermined length; and
wherein the liquid introduced from the inlet flows upward while forming the swirl and is discharged from the outlet.

2. The medical liquid-pressure-detecting device according to claim 1, wherein the positive-pressure-detecting region is a central region of the diaphragm that projects toward the liquid chamber, and the negative-pressure-detecting region is a region of the diaphragm that projects toward the gas chamber between a peripheral edge and the positive-pressure-detecting region.

3. The medical liquid-pressure-detecting device according to claim 2, wherein the negative-pressure-detecting region and the positive-pressure-detecting region each form an arc shape projecting downward or an arc shape projecting upward and are gently continuous with each other.

4. The medical liquid-pressure-detecting device according to claim 3, wherein the chamber unit has a spherical shape, and the negative-pressure-detecting region and the positive-pressure-detecting region come into close contact with an inner wall of the chamber unit when a negative pressure or a positive pressure that is greater than predetermined is generated in the liquid stored in the liquid chamber.

5. The medical liquid-pressure-detecting device according to claim 4, wherein the diaphragm when deformed by a negative pressure in the liquid chamber extends over the inlet, and the liquid introduced from the inlet flows upward while forming the swirl and is discharged from the outlet when the inlet is not covered by the diaphragm.

6. The medical liquid-pressure-detecting device according to claim 1, wherein the negative-pressure-detecting region and the positive-pressure-detecting region have a substantially uniform thickness.

7. The medical liquid-pressure-detecting device according to claim 1, wherein the chamber unit includes a connecting portion that is connectable to a sensor unit for detecting a change in a pressure of the gas stored in the gas chamber, and the connecting portion includes a sealing member that seals a connected portion of the sensor unit and into which the connected portion is fittable, and a communication hole into which the connected portion is insertable.

8. The medical liquid-pressure-detecting device according to claim 7, wherein the sensor unit communicates with the gas chamber of the chamber unit through the connecting portion so that the sensor unit is capable of detecting a change in pressure of gas stored in the gas chamber.

9. The medical liquid-pressure-detecting device according to claim 7, wherein the chamber unit includes a stay that secures the sensor unit and the connected portion at a predetermined position of a blood purification apparatus, and the senor unit includes a wall portion that covers and protects an outer periphery of the connected portion.

10. A liquid flow route to which the medical liquid-pressure-detecting device according to claim 1 is connected.

11. A medical apparatus comprising the liquid flow route according to claim 10.

12. The medical liquid-pressure-detecting device according to claim 1, wherein the positive-pressure-detecting region and the negative-pressure-detecting region are continuous from the center towards a peripheral edge of the diaphragm.

13. The medical liquid-pressure-detecting device according to claim 1, wherein the diaphragm is made of a soft air-permeable material.

14. The medical liquid-pressure-detecting device according to claim 1, wherein the diaphragm is made of silicon, styrene-ethylene-butylene-styrene (SEBS), or isoprene.

15. The medical liquid-pressure-detecting device according to claim 1, wherein the negative-pressure-detecting region and the positive-pressure-detecting region come into close contact with an inner wall of the chamber unit when a negative pressure or a positive pressure respectively is generated due to a spherical shape of the chamber unit.

16. A medical liquid-pressure-detecting device comprising:
a chamber unit connected to a liquid flow route and having:
an inlet from which liquid flowing in the flow route is taken in and
an outlet from which the liquid is discharged, the chamber unit being capable of storing the liquid by a predetermined amount while the liquid flows from the inlet to the outlet; and
a diaphragm dividing an inside of the chamber unit into a liquid chamber that stores the liquid and a gas chamber that stores a predetermined gas, the diaphragm being deformable in accordance with a pressure of the liquid in the liquid chamber,
the medical liquid-pressure-detecting device being capable of detecting a pressure of the liquid in the flow route on a basis of a change in the pressure in the gas chamber that is caused by the deformation of the diaphragm,
wherein the diaphragm includes:
a negative-pressure-detecting region that deforms toward one side when a negative pressure is generated in the liquid stored in the liquid chamber, and
a positive-pressure-detecting region that has a region projecting upward at a center of the diaphragm and is positioned below a center of a swirl of the liquid that is generated when the liquid flows from the inlet to the outlet and the positive-pressure-detecting region deforms toward an other side when a positive pressure is generated in the liquid stored in the liquid chamber; and
wherein the outlet is provided at a top of the liquid chamber of the chamber unit and at a center position in a widthwise direction, and the inlet is provided at a position of the liquid chamber that is lower than the outlet is shifted from a center position in the widthwise direction by a predetermined length; and
wherein the diaphragm when deformed by a negative pressure in the liquid chamber extends over the inlet.

17. The medical liquid-pressure-detecting device according to claim 16, wherein the liquid introduced from the inlet flows upward while forming the swirl and is discharged from the outlet.

18. The medical liquid-pressure-detecting device according to claim 17, wherein the liquid introduced from the inlet flows upward while forming the swirl and is discharged from the outlet when the inlet is not covered by the diaphragm.

19. The medical liquid-pressure-detecting device according to claim 16, wherein the diaphragm is made of silicon, styrene-ethylene-butylene-styrene (SEBS), or isoprene, and the positive-pressure-detecting region and the negative-pressure-detecting region are continuous from the center towards a peripheral edge of the diaphragm.

20. The medical liquid-pressure-detecting device according to claim 16, wherein the chamber unit includes a connecting portion that is connectable to a sensor unit for detecting a change in a pressure of the gas stored in the gas chamber, and the connecting portion includes a sealing member that seals a connected portion of the sensor unit and into which the connected portion is fittable, and a communication hole into which the connected portion is insertable, and wherein the sensor unit communicates with the gas chamber of the chamber unit through the connecting portion so that the sensor unit is capable of detecting a change in pressure of gas stored in the gas chamber.

* * * * *